(12) United States Patent
Sehgal et al.

(10) Patent No.: US 11,071,517 B2
(45) Date of Patent: Jul. 27, 2021

(54) MACHINE IMPLEMENTED METHODS, SYSTEMS, AND APPARATUSES FOR IMPROVING DIAGNOSTIC PERFORMANCE

(71) Applicant: The Trustees of The University of Pennsylvania, Philadelphia, PA (US)

(72) Inventors: Chandra M. Sehgal, Wayne, PA (US); Santosh S. Venkatesh, Swarthmore, PA (US); Laith R. Sultan, Exton, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 905 days.

(21) Appl. No.: 15/341,269

(22) Filed: Nov. 2, 2016

(65) Prior Publication Data

US 2017/0140124 A1    May 18, 2017

Related U.S. Application Data

(60) Provisional application No. 62/253,314, filed on Nov. 10, 2015.

(51) Int. Cl.
| | |
|---|---|
| *A61B 8/08* | (2006.01) |
| *A61B 5/00* | (2006.01) |
| *G16H 50/30* | (2018.01) |
| *G16H 30/20* | (2018.01) |
| *G16H 50/20* | (2018.01) |

(52) U.S. Cl.
CPC .......... *A61B 8/0825* (2013.01); *A61B 5/4312* (2013.01); *A61B 5/7275* (2013.01); *A61B 8/085* (2013.01); *A61B 8/5223* (2013.01); *G16H 30/20* (2018.01); *G16H 50/20* (2018.01); *G16H 50/30* (2018.01)

(58) Field of Classification Search
CPC ........ G16H 50/70; G16H 50/30; G16H 10/60; G16H 50/20
See application file for complete search history.

(56) References Cited

U.S. PATENT DOCUMENTS

| | | | | |
|---|---|---|---|---|
| 5,677,966 | A * | 10/1997 | Doerrer | G01N 15/1475 382/128 |
| 2001/0043729 | A1 * | 11/2001 | Giger | G06F 19/321 382/128 |
| 2003/0174873 | A1 * | 9/2003 | Giger | G06T 7/0012 382/128 |
| 2004/0077944 | A1 * | 4/2004 | Steinberg | A61B 5/0536 600/436 |
| 2008/0052007 | A1 * | 2/2008 | Yu | C12Q 1/6886 702/20 |

(Continued)

FOREIGN PATENT DOCUMENTS

WO    WO-2013049153 A2 *    4/2013    .......... A61B 5/4381

*Primary Examiner* — John P Go
(74) *Attorney, Agent, or Firm* — BakerHostetler

(57) ABSTRACT

A method for ultrasound diagnosis includes determining a first risk of malignancy based on a human assessment of a first set of features of one or more ultrasound images of a target; determining a second risk of malignancy based on an automatically extracted second set of features of the one or more ultrasound images; determining at least one overall risk value based on the first risk of malignancy and the second risk of malignancy; and characterizing the at least one overall risk value as one of a high confidence assessment or a low confidence assessment.

14 Claims, 12 Drawing Sheets

(56) References Cited

U.S. PATENT DOCUMENTS

| | | | |
|---|---|---|---|
| 2010/0087756 A1* | 4/2010 | Egorov | A61B 5/0053 600/587 |
| 2010/0098306 A1* | 4/2010 | Madabhushi | G06T 7/0012 382/128 |
| 2010/0292571 A1* | 11/2010 | Kim | A61B 5/02007 600/438 |
| 2012/0095331 A1* | 4/2012 | Ohashi | G06T 7/0014 600/425 |

* cited by examiner

MACHINE IMPLEMENTED METHODS, SYSTEMS, AND APPARATUSES FOR IMPROVING DIAGNOSTIC PERFORMANCE

CROSS-REFERENCE TO RELATED APPLICATION

This application claims the benefit of U.S. Provisional Application No. 62/253,314, filed Nov. 10, 2015, the contents of which are incorporated herein by reference in their entireties for all purposes.

STATEMENT REGARDING FEDERALLY SPONSORED RESEARCH

This invention was made with government support under RO1CA130946 awarded by the National Institutes of Health. The government has certain rights in the invention.

FIELD OF THE INVENTION

This disclosure relates to machine implemented methods for improving diagnostic performance as well as systems and apparatuses using the same.

BACKGROUND OF THE INVENTION

There is an ongoing effort in improving breast ultrasound for differentiating solid malignant and benign masses. Despite advances in both breast imaging technology and image analysis, the biopsy yield continues to be low and as many as 70% to 85% of biopsies prove to be benign. One of the main reasons for such low yield is that the false negatives have major consequences related to patient mortality. The cost of this low yield results in unnecessary trauma experienced by patients (having masses biopsied which are ultimately determined to be benign) and the financial burden imposed by a large number of unneeded procedures.

SUMMARY OF THE INVENTION

Aspects of the invention relate to methods, systems and apparatuses implementing machine apparatuses for improving diagnostic performance.

In accordance with one aspect of the invention, a method is provided for a machine implemented method for ultrasound diagnosis. The method includes determining a first risk of malignancy based on a human assessment of a first set of features of one or more ultrasound images of a target; determining a second risk of malignancy based on an automatically extracted second set of features of the one or more ultrasound images; determining at least one overall risk value based on the first risk of malignancy and the second risk of malignancy; and characterizing the at least one overall risk value as one of a high confidence assessment or a low confidence assessment.

In accordance with another aspect of the invention, an system is provided for diagnosing a tumor using an imaging scan of a target. The system includes an imaging system configured to perform an imaging scan of a target and to obtain imaging information regarding the target; and a processing system configured to receive the imaging information from the imaging system and to extract a second set of features of the imaging information. The processing system is further configured to receive a human assessment of the imaging information, wherein the human assessment of the imaging information is based on a first set of features of the imaging information. Additionally, the processing system is configured to determine an overall risk value based on an analysis of the second set of features and the human assessment of the first set of features.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. Included in the drawings are the following figures.

DETAILED DESCRIPTION OF THE INVENTION

The inventors recognized that diagnostic performance may be improved by completing multiple readings of an imaging scan of a suspected target abnormality, such as a cancerous tumor. In particular, the inventors recognized that by correlating a human assessment of one or more images with a second, computer generated assessment of the images, superior diagnostic performance may be obtained by methods, systems, and apparatuses for diagnosing target masses.

The present invention may be employed to improve the diagnostic performance of any image that is assessed to diagnosis or treat patients such as, e.g., ultrasound images, MRI images, X-ray images, electroencephalography, magnetoencephalography, and electrocardiography. While the examples herein may refer to ultrasound imaging, one of ordinary skill in the art, upon reading this disclosure, will understand that the principles described herein are not so limited and may be applied to any imaging modality.

Figure 1:
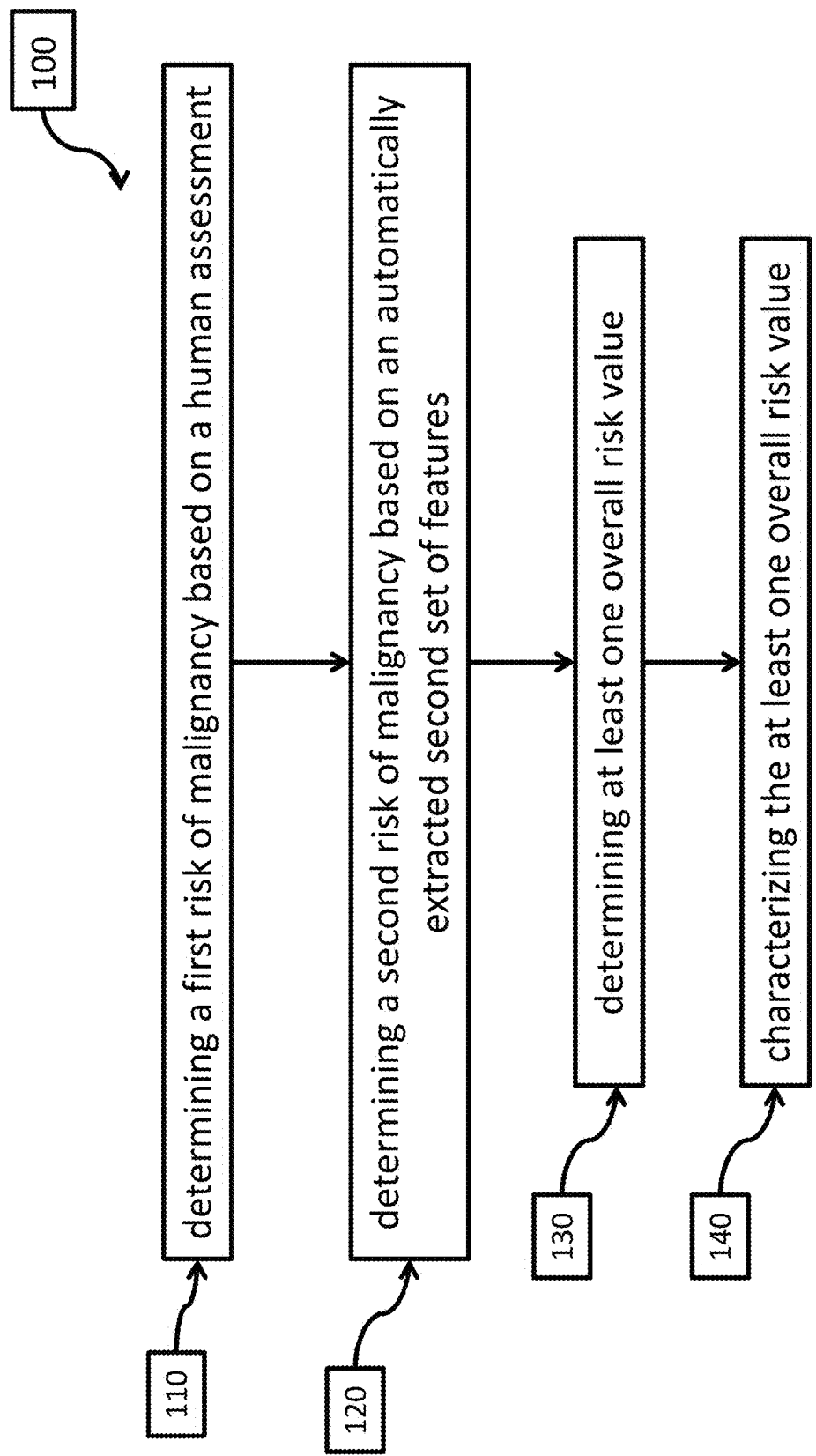
FIG. 1 is a flow diagram of a machine implemented method for improving diagnostic performance in accordance with aspects of the invention.

FIG. 1 depicts a machine implemented method 100 for improving diagnostic performance. As a general overview, method 100 includes determining a first risk of malignancy, determining a second risk of malignancy, determining at least one overall risk value, and characterizing the at least one overall risk value.

In step 110, a first risk of malignancy is determined by human assessment. The human observer may extract a first set of features from the image of a target (e.g. a tumor, lesion, biological mass, etc.). Based on the first set of features, the human observer may determine a risk of malignancy. The first set of features may include any characteristics or features of being malignant or benign that may be used by one of skill in the art. The human assessment may include rating each of the features on a binary scale (e.g., presence or absence) or on a multilevel scale to indicate the level of confidence in the presence of the feature.

In step 120, a second risk of malignancy is determined based on an automatically extracted second set of features. A data processor may be employed to extract the second set of features from the same images analyzed by the human observer or from different images of the target. The data processor may extract values for features such as grayscale, shape, coarseness of a margin, texture of a lesion, information based on Doppler effects, elastography, etc. Other machine-extractable features for determining if a tumor is malignant or benign may be used without departing from the spirit of the invention disclosed herein. The data processor may employ stored images, e.g. a library of images, with known diagnoses to facilitate determination of the second risk of malignancy based on the automatically extracted second set of features.

In one embodiment, more than two sets of features may be used to generate additional determinations of risk of malignancy, thereby enhancing the accuracy of the overall risk value.

The target may be segmented by an automated, semi-automated, or manual tracing of the target. Segmentation of the target may facilitate the precision and/or extraction of the second set of features by the data processor. In one embodiment, the target is partitioned into sectors to facilitate extraction of the first and/or second set of features. For example, the target may be partitioned into sectors, whereby each sector is analyzed separately and/or compared to each other. Partitioning of the target may also be automated, semi-automated, or based on manual identification of sectors.

Method 100 may include applying a classifier to the sets of features extracted by the human observer and/or the data processor. In one embodiment, the classifiers model an underlying chance that the target is malignant ("M") or that the target is benign ("B"). The classifiers may be selected to match the characteristics in the extracted set of features. The classifiers weigh the extracted features and determine a first risk of malignancy based on the first extracted set of features and/or a second risk of malignancy based on the second extracted set of features. Exemplary classifiers include, e.g., logistic regression, Naïve Bayes, continuous, ordinal, nominal, spatial, and frequency classifiers.

In step 130, at least one overall risk value is determined. The overall risk value may be based on combining the first risk of malignancy and the second risk of malignancy.

In another embodiment, method 100 employs an adaptive learning analysis that improves the classifiers' determination of a risk of malignancy. The adaptive learning analysis may be employed to correlate the determined first risk of malignancy and the second risk of malignancy, thereby determining the overall risk value. For example, the adaptive learning analysis may be employed to analyze the first set of features to determine the first risk of malignancy and/or the second set of features to determine the second risk of malignancy. In one embodiment, the adaptive leaning analysis is applied to both the first and second set of features and/or the first and second classifiers, thereby correlating and relying upon the stronger indications of malignancy or benignness identified by the two sets of features. The adaptive learning analysis may minimize the exponential loss criterion on the set of features by using a forward, stage-wise additive model to combine multiple constituent classifiers. In one embodiment, the adaptive learning analysis is the Adaptive Boosting process.

Adaptive learning analysis may be used to examine the independent diagnosis of the first classifier and the second classifier. For example, the adaptive learning analysis may assess the definitiveness of diagnosis by measuring the distance from a mid-probability of 0.5. Assessments that have less definitive diagnosis by on one classifier regarding one or more features receive greater weight in the final diagnosis from the second classifier regarding those same one or more features, thereby improving performance.

In one embodiment, the adaptive learning analysis begins with a tabula rasa in which the elements of the set of features are weighted equally. In the first iteration of analysis, the first classifier in the sequence is applied on the uniformly weighted elements and, at the end of the iteration, the sample elements are reweighted with greater weight placed on those elements that the classifier found difficult to label correctly. The iterations now proceed in a sequence of rounds, each constituent classifier is applied sequentially on a reweighted set of elements with greater weight placed on the elements that the previous classifier in the sequence found difficult to classify accurately. At the end of each iteration of analysis, the sample error (or, more precisely, the risk) of the classifier being applied on the (reweighted) set of features or elements thereof is recorded before the elements are reweighted yet again and analyzed by the next classifier in the sequence of iterations. The final boosted classifier forms its prediction as a convex combination of the predictions of each constituent classifier, the more accurate classifiers (with respect to iteration error) given more weight.

In step 140, the at least one overall risk value is characterized as either a high confidence or low confidence assessment. The characterization of high confidence or low confidence refers to a statistical likelihood that the overall risk value accurately indicates whether the target is benign or malignant. To further improve the diagnostic performance of method 100, low confidence assessments may undergo further imaging and/or evaluation. For example, in one embodiment, when the overall risk value is characterized as being a low confidence assessment, method 100 includes additional imaging of the target. In another embodiment, when the overall risk value is characterized as being of low confidence, method 100 includes a biopsy of the target. In yet another embodiment, method 100 indicates that further evaluation of the target may be warranted when the overall risk value is characterized as a low confidence assessment.

The assessment may be characterized as high confidence or low confidence by comparing the overall risk value to an ambiguity threshold range and if the at least one overall risk value falls within the ambiguity threshold range, characterizing the at least one overall risk value as a low confidence assessment. Additionally or alternatively, an overall risk value may be characterized as a low confidence assessment if the two risk of malignancies indicate different outcomes. For example, if one risk of malignancy indicates that the target is benign and the other risk of malignancy indicates that the target is malignant, than the overall risk value may be characterized as a low confidence assessment.

Figure 2:
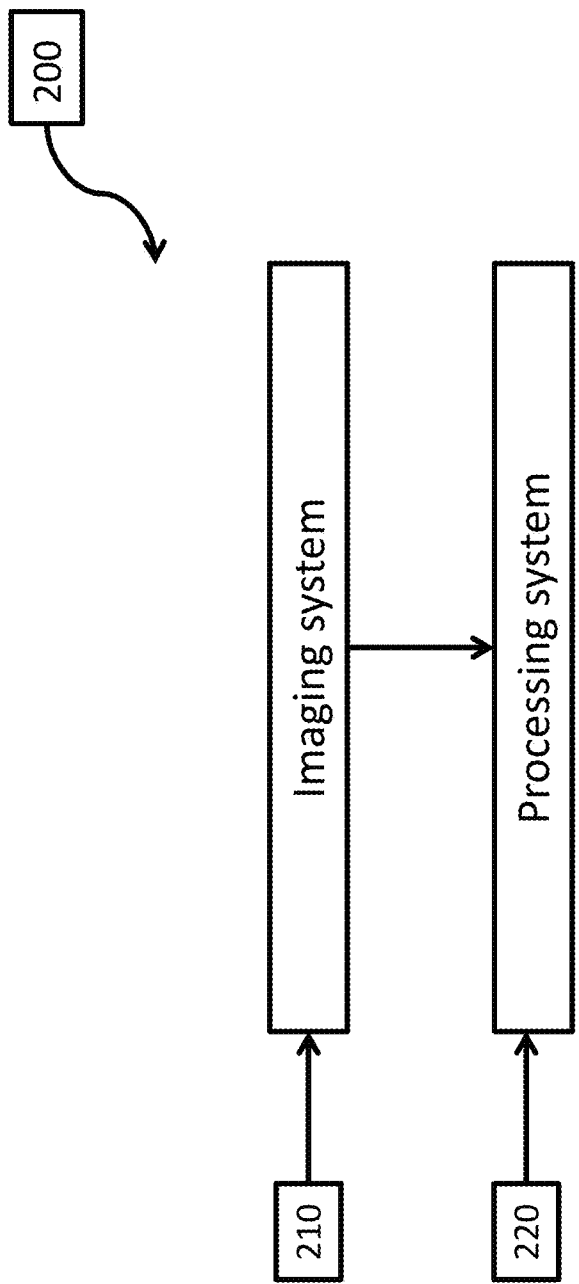
FIG. 2 is a schematic of a system for improving diagnostic performance according to aspects of the invention.

FIG. 2 depicts a system 200 for diagnosing a tumor using an imaging scan of a target. As a general overview, system 200 includes a imaging system 210 and a processing system 220. System 200 may include, for example, an ultrasound diagnosis apparatus configured to employ method 100.

Imaging system 210 is configured to perform an imaging scan of a target (e.g., a tumor and/or biomass) and to obtain imaging information regarding the target. Imaging system 210 may include any imaging modality, e.g., an ultrasound system, MRI system, X-ray system, electroencephalography system, magnetoencephalography system, electrocardiography system, etc. The imaging system 210 may be integrally connected to processing system 220 or may be remotely connected by way of a local area network (LAN), a wireless network, a satellite communication network, a landline telephone network, or other suitable network to facilitate two way communication between imaging system 210 and processing system 220. In one embodiment, however, imaging system 210 is not connected to processing system 220, but merely provides images that may be subsequently provided to processing system 220.

Processing system 220 is configured to receive the imaging information from imaging system 210 and to extract a second set of features from the imaging information. Processing system 220 may automatically, semi-automatically, or require manual identification of one or more features to extract the second set of features. In one embodiment, processing system 220 automatically extracts the second set of features after the target is partitioned. Preferably, processing system 220 is configured to automatically or semi-automatically partition the target.

Processing system 220 may be further configured to receive a human assessment of the imaging information, wherein the human assessment of the imaging information is based on a first set of features of the imaging information. For example, a physician or imaging technician may assess physiological data from the imaging information and report these assessments to processing system 220 using an interface located at or remote from imaging system 210.

Preferably, the processing system 220 is configured to determine an overall risk value based on an analysis of the second set of features and the human assessment of the first set of features.

System 200 may further characterize the overall risk value as being a high confidence assessment or a low confidence assessment. For example, system 200 may be configured to indicate by way of sound, image, or other type of notification, that the overall risk value is a low confidence assessment and/or high confidence assessment. In one embodiment, system 200 is configured to run additional evaluation of the target, if the overall risk value is characterized as a low confidence assessment. Determination of whether the overall risk value is of high confidence or low confidence may be based on whether the first risk of malignancy and the second risk of malignancy are consistent with each other or may be based on comparing the overall risk value to an ambiguity threshold.

EXAMPLES

The following examples are a non-limiting embodiment of the present invention, included herein to demonstrate the potential of aspects of the present invention.

Example 1

Figure 12:
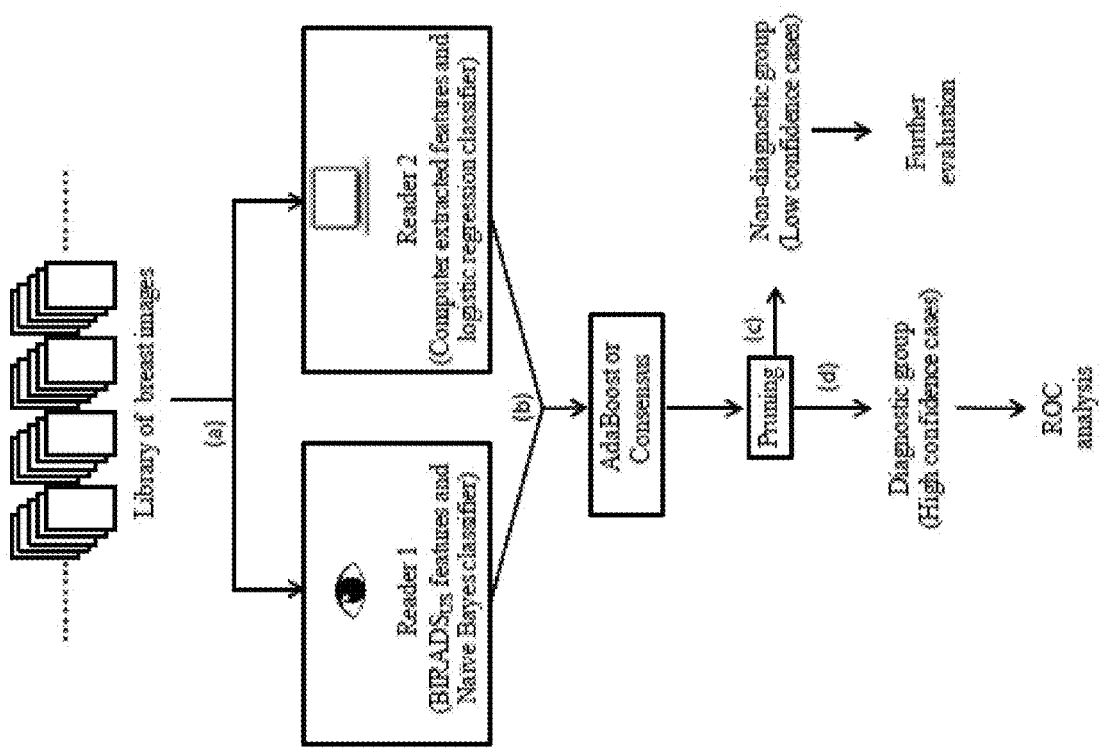
FIG. 12 is a schematic of the machine implemented method employed in the example for improving diagnostic performance according to aspects of the invention.

FIG. 12 generally depicts the method employed in this example. Two independent sets of features were extracted and classified from each image in the library of breast ultrasound images, one set being extracted by a radiologist's interpretation of ultrasound BIRADS (BI-RADS$_{us}$) and one set of features extracted by way of a computer from the images (FIG. 12, step a). The radiologist's interpretations of ultrasound images (BI-RADS$_{us}$) could be combined with the computer-identified features using adaptive boosting or a consensus method, described below (FIG. 12, step b). This process was implemented to expand the discriminatory region of each feature set by incorporating the strengths of each set of features. Despite combining the regions of strength of each of the two independent feature sets some assessments remained characterized as being a low confidence assessment. These low confident assessments were removed from the dataset for further evaluation by additional imaging (FIG. 12, step c). The remaining assessments, representing high confidence group, were evaluated for their diagnostic performance (FIG. 12, step d).

To ensure the accuracy of results, the images were reviewed independently by two physicians (hereafter "Observer 1" and/or "Observer 2") using ACR guidelines (ACR 2003) to produce two sets of human assessment for the risk of malignancy. The observers were not privy to other patient information including age, medical history, and biopsy results. The BI-RADS$_{us}$ features consisted of ten different features that characterize margin properties, echo patterns, posterior shadowing, and enhancement of the lesions.

Figure 3B:
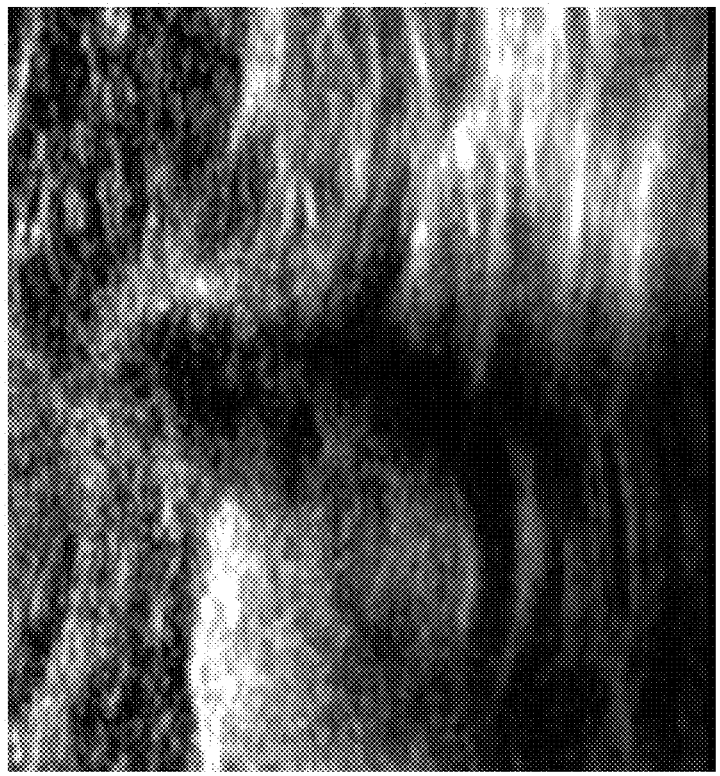
FIG. 3B is an ultrasound image of a tumor with malignant features.
Figure 3A:
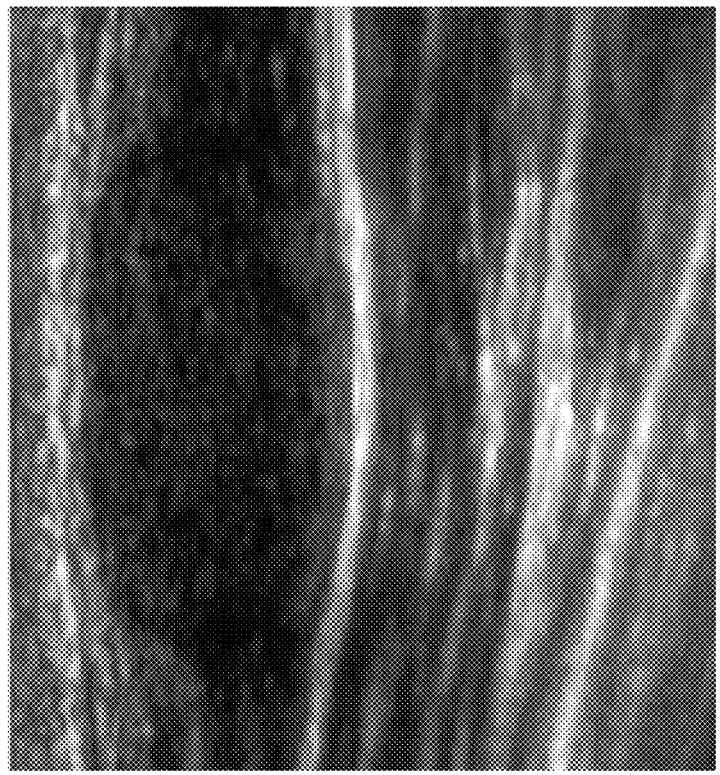
FIG. 3A is an ultrasound image of a tumor with benign features.

The library of images included five to seven views produced by sonographic images for each target (e.g. mass and/or tumor) in radial and anti-radial planes. FIGS. 3A and 3B show examples of breast masses with malignant and benign characteristics.

Each of the patients in this example also underwent a biopsy. The results of the biopsy were compared to the results of the method employed herein to determine the accuracy of said method. Of the 264 masses 179 and 85 were designated as benign and malignant, respectively. Among the malignant lesions (76%) were invasive carcinoma, (8%) were invasive lobular carcinoma, (8%) were ductal carcinoma in situ; and (4%) were adenocarcinoma. The remaining 4% were mixed including poorly differentiated carcinomas and mucinous mammary carcinoma. Of the benign masses, 44% were fibroadenoma, 33% had miscellaneous fibrocystic changes, 6% were sclerosing adenosis, and the remaining 17% were benign lesions without atypia in the histopathology report. The mean age of all the patients studied was 51.5±14.7 years.

Two qualitatively different types of features were extracted from images (e.g. sonograms in this example). The first type consisted of ultrasound BI-RADS$_{us}$ features that are used routinely for evaluating suspicious breast lesions in breast ultrasound images. BI-RADS$_{us}$ is the standardized lexicon proposed by American College of Radiology (ACR) for reporting and characterizing breast masses (ACR 2003).

The second set of features was extracted by an automated procedure from manual tracings. For each breast ultrasound image reviewed by the physicians the lesion was manually traced on a computer display using a mouse. Eight features describing grayscale, shape, and coarseness of the margin were automatically computed from the traced margin. These features were extracted by partitioning the lesion into N sectors and then comparing the difference between the inside and the outside of each sector. The features used in the analysis included the brightness difference between the lesion interior and immediate exterior, margin sharpness, angular variation in brightness, depth-to-width ratio, axis ratio, tortuosity, radius variation, and elliptically normalized skeleton. In addition to ultrasound image features, patient age and mammographic BI-RADS$_{us}$ (categories 1-5 representing probabilities of increasing malignancy) were also included in the analysis completed by the computer.

From the image of each lesion a set of features F=F$_1$, F$_2$, ..., F$_N$ were extracted. These extracted features constituted the "measurements" representing the characteristics of the underlying lesions.

Two types of classifiers were applied to determine the accuracy and/or precision of each classifier. The Naïve Bayes formulation was applied as a classifier. In the Naive Bayes formulation the features are assumed to be conditionally independent. In the case of nominal features, discrete values were expressed mathematically as $$P(F_1, F_2, \ldots, F_N | M) = P(F_1 | M) \times P(F_2 | M) \times \ldots \times P(F_N | M)$$

where an expression of the form P(•|•) stands for a conditional probability with P(•) representing an unconditional probability. Pursuant to Bayes' rule, the a posteriori probability of malignancy is given by $$P(M|F) = \frac{1}{z} P(M) \prod_{j=1}^{N} P(F_j | M)$$

where, by total probability, we may write the normalizing constant Z representing the unconditional probability of observing the given features in the form $$Z = P(F) = P(F|M)P(M) + P(F|B)P(B).$$

The quantities P(M) and P(B) constitute a priori probabilities in the Bayesian settings of malignant and benign assessments. These probabilities are not known ahead of time but are estimated in the usual way by the relative frequency of occurrence (malignancy) in the training data set.

The Logistic Regression formulation was also applied as a classifier to determine the accuracy and/or precision of such classifier. Logistic regression models arise in settings where features take a continuum of values in a finite-dimensional space out of a desire to have the a posteriori class probabilities expressible in terms of simple linear functions of the features. Formally, the logarithm of the odds ratio is assumed to be in the form $$\log \frac{P(M|F)}{P(B|F)} = c_0 + \sum_{j=1}^{N} c_j F_j$$

which, in view of the fact that P(B|F)=1−P(M|F), we may express as $$P(M|F) = \frac{1}{1 + \exp(-z(F))}$$

where z(F) is given by the linear form $$z(F) = c_0 + \Sigma_{j=1}^{N} c_j F_j.$$

Advantageously, this classifier may be applied while only evaluating the linear parameters $c_0, c_1, \ldots, c_N$. Additionally, the Logistic Regression classifier is well suited for the continuous nature of the set of features extracted automatically by the data processor. Similar to BI-RADS$_{us}$ data training and testing was performed by leave-one-out cross-validation. In this Example, leave-one-out cross-validation was employed by training N−1 samples of the dataset to predict the probability of the remaining Nth sample. The prediction was compared with the biopsy results. The process was employed with each sample tested in this Example.

In this example, the first risk of malignancy, which was determined by human assessment, and the second risk of malignancy, which was automatically determined, were combined using an adaptive learning analysis to determine real-valued outcomes. Here, the adaptive learning analysis was Adaptive Boosting (hereafter "AdaBoost").

The representation of a lesion in feature space and its (biopsy-certified) label form a pair (x, y) where x represents a feature vector and y is the associated label. In our current context of features extracted by two readers we may represent the feature vector in the form x=(F$^{(1)}$ F$^{(2)}$) where F$^{(1)}$=F$_1^{(1)}$, ..., F$_{N1}^{(1)}$ represents the collection of (nominal-valued) BI-RADS$_{us}$ features and F$^{(2)}$=F$_1^{(2)}$, ..., F$_{N2}^{(2)}$ represents the collection of (continuum-valued) computer-generated features. The associated label y takes one of two numeric values, 1 representing malignant (M), and 0 representing benign (B). In this setting a real-valued classifier is a function f(x) which maps each vector x in feature space into a real value which nominally represents the classifier's estimate of the a posteriori probability of malignancy conditioned on the observed feature vector x. One desirable goal in classifier design is to minimize, in some suitable sense, the error $$|f(x) - y|.$$

Let f1(F$^{(1)}$) and f$_2$(F$^{(2)}$) represent the outputs of the Naive Bayes and Logistic Regression classifiers operating on their respective feature sets. While, nominally, each of these classifiers operates on the entire feature space x=(F$^{(1)}$, F$^{(2)}$), in practice they have been selected to match the characteristics of the two rather different types of features that have been generated. Accordingly, the Naive Bayes classification f$_1$(x)=f$_1$(F$^{(1)}$) depends only on the nominal BI-RADSus features F$^{(1)}$=F$_1^{(1)}$, ... F$_N^{(1)}$, while, in a similar fashion, the Logistic Regression classification f(x)=(F$^{(2)}$) depends only on the computer-generated features F$^{(2)}$=F$_1^{(2)}$, ..., F$_{N2}^{(2)}$. Thus, each of these classifiers operates in a natural lower-dimensional subspace of the entire feature space. We may view these procedures in a formal sense as using domain knowledge to reduce both the effective dimensionality of the feature space and the effective complexity of the resulting classifier f(•) obtained by boosting from $f_1(•)$ and $f_2(•)$. This in effect accomplishes a "practitioner's complexity regularization" by using domain knowledge to mitigate both Bellman's curse of dimensionality as well as the danger of overfitting.

The boosted classifier f(•) is obtained from the constituent classifiers $f_1(•)$ and $f_2(•)$ by training on a random sample of data $(x_1, y_1), (x_2, y_2), \ldots, (x_n, y_n)$ obtained (presumptively) by independent sampling from an underlying probability distribution governing the class-conditional distribution of features and the a priori probabilities of the two classes in the population at large. We train first on the Naive Bayes classifier $f_1(•)$ and then on the Logistic Regression classifier $f_2(•)$. The order may of course be reversed without any essential change in the algorithm.

In the first iteration, equal weight is placed on each element of the set of features:

$$w_{1,j} = \frac{1}{n} \text{ for } 1 \leq j \leq n.$$

The classifier $f1$ is fitted to the training data using weights w1, where fitting is with respect to the squared error. The optimum classifier $f1$ is selected (in our case from the class of Naïve Bayes classifiers) and its weighted (minimum) squared error computed: $\text{err}_1 = \Sigma_{j=1}^n w_{1,j} |f_1(x_j) - y_j|^2$. The weight (or importance) c1 of classifier $f1$ is now deduced from the squared error via the logarithm of the odds ratio, $$c_1 = \frac{1}{2} \ln\left(\frac{1 - \text{err}_1}{\text{err}_1}\right).$$

Round 2 (the final round of iterations in this example) begins with a reweighting of the sample elements. For $1 \leq j \leq n$, the data point $(x_j, y_j)$ is given weight $$w_{2,j} = \frac{w_{1,j} e^{c_1 |f_1(x_j) - y_j|^2}}{z_1}$$

where $Z_1$ is a normalization factor chosen so that the sum of the weights is 1. The second classifier $f_2$ is now fitted to the training data using weights $w_2j$, fitting again with respect to squared error. The squared error $\text{err}_2$ and the weight (importance) $c_2$ of the best Logistic Regression classifier $f_2$ are now computed by analogous formulae, $$\text{err}_2 = \sum_{j=1}^n w_{2,j} |f_2(x_j) - y_j|^2 \text{ and } c_2 = \frac{1}{2} \log\left(\frac{1 - \text{err}_2}{\text{err}_2}\right).$$

This concludes the iterations. It should be noted that, without loss of generality, we may assumed err1 and $\text{err}_2$ are both $<\frac{1}{2}$ (if necessary, by interchanging the roles of 0 and 1) so that the classifier weights $c_1$ and $c_2$ are both positive. The AdaBoost classifier f is formed as a convex combination of the two constituent classifiers $f_1$ and $f_2$ weighted in accordance with their relative importance $c_1$ and $c_2$, respectively. Thus, we set $$f(x) = \frac{c_1}{c_1 + c_2} f_1(x) + \frac{c_2}{c_1 + c_2} f_2(x).$$

In the standard mode of operation, once the AdaBoost classifier f is determined, a hard-limited classification of a given lesion with feature vector x is made by selecting a threshold t of operation and mapping x to 1 (malignant) or 0 (benign) in accordance with whether $f(x) > t$ or $f(x) \leq t$, respectively. By varying t it is possible to obtain the ROC curve characteristic of the classifier. In this example, the error function was modified to account for the continuous nature of the classifiers used, and to limit over-weighting assessments with a large difference between the predicted and actual outcome.

The AdaBoost classifier output f(x) represented an estimate of the a posteriori probability of malignancy for a given a vector of features x. Accordingly, values near 0 or 1 represented high confidence assessments that were benign or malignant, respectively, while values near ½ represented ambiguous assessments that should be further evaluated by other imaging methods.

An ambiguity threshold range was selected by specifying an ambiguity interval $(t_l, t_u)$ with a lower threshold $t_l$ and an upper threshold $t_u$. Lesions for which the feature vector x satisfies $t_l < f(x) < t_u$, were characterized as a low confidence assessment and, thus, removed/set aside for further testing by other imaging methods. On the other hand, lesions for which the feature vector x was outside the ambiguity threshold range were recorded as 1 or 0 depending on whether $f(x) > t_u$ or $f(x) < t_i$, respectively. With the ambiguity threshold range centered on ½ (corresponding to the maximum uncertainty) drop rate was determined for different ambiguity intervals. The drop rate is number of assessments that are identified for further imaging. As low confidence assessments will require additional testing, the drop rate stands in the role of a quantifiable surrogate for a cost; the performance of the classifier on the disambiguated assessments that are retained provides a second quantifiable attribute. Hence applying a ambiguity threshold range operates effectively in a two-dimensional cost performance rubric and allows users to achieve desired level of performance or drop rates by varying the location and size and of the ambiguity interval.

As an alternatively method for characterizing the confidence of the assessment, the inventors believe a consensus method may provide suitable advantages. Under the proposed consensus method assessments having a first risk of malignancy and a second risk of malignancy that are contradictory are characterized as low confidence, while assessments having both the first and second risk of malignancies indicating that the target is malignant or bingeing are characterized as high confidence.

Figure 4:
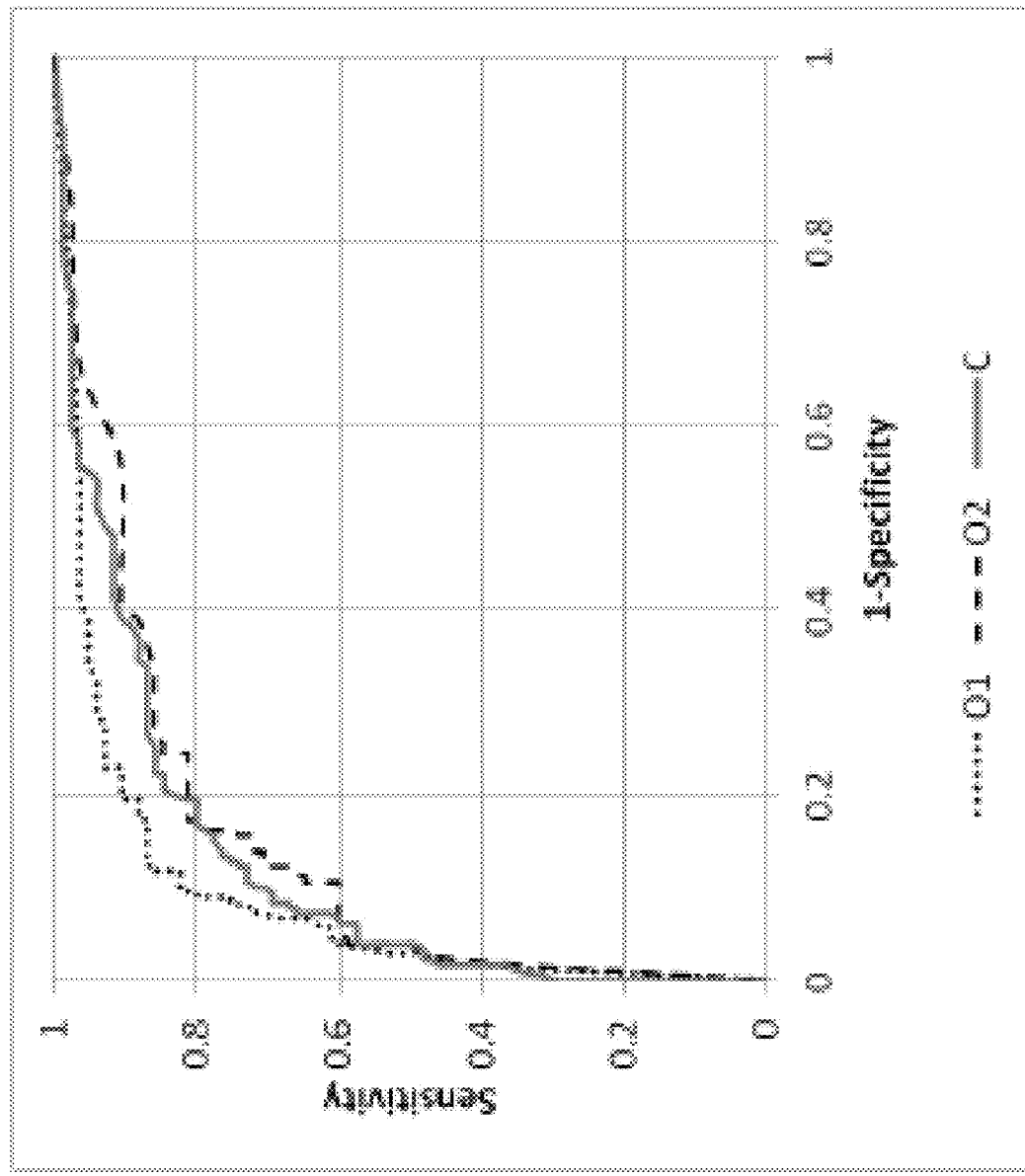
FIG. 4 is a graph illustrating the performance of two human observers and a computer-based image analysis according to aspects of the invention.

The methods employed in this Example provided highly advantageous results. Both visual and computer features were high performers with area under the ROC curve $(A_z)$ ranging between 0.866 to 0.924 (Rows A and B, Table 1). The area under the ROC curve, $A_z$, for the two observers was markedly different, 0.924 for Observer 1 versus 0.866 for Observer 2, with Observer 2 underperforming Observer 1 in all parts of the curve (FIG. 4). The difference of 0.058 in $A_z$ between the two observers was significant (p=0.006).

The ROC curve for computer features was in between the performance of the two observers; $A_z$ for computer features was lower than that of Observer 1, 0.887 vs. 0.924, but higher than that of Observer 2, 0.887 vs. 0.866. The difference in $A_z$ between observers and the computer analysis was not significant: p=0.334 for Observer 1 vs. computer and p=0.279 for Observer 2 vs. computer.

Combining visual and computer features with AdaBoost increased $A_z$ for both observers: 0.924 to 0.937 for Observer 1 and 0.866 to 0.905 for Observer 2 (Rows C and D, Table 1). The difference in performance between the observers was reduced to 0.031 after boosting compared to the difference of 0.058 observed without boosting. The improvement in performance after boosting was significant (p=0.016). The $A_z$ values obtained by taking visual features first, followed by computer-generated features was comparable to those obtained by taking computer generated features first, followed by visual features: 0.937 and 0.936 for Observer 1 and 0.906 and 0.905 for Observer 2 (Rows C and D, Table 1).

Figure 5:
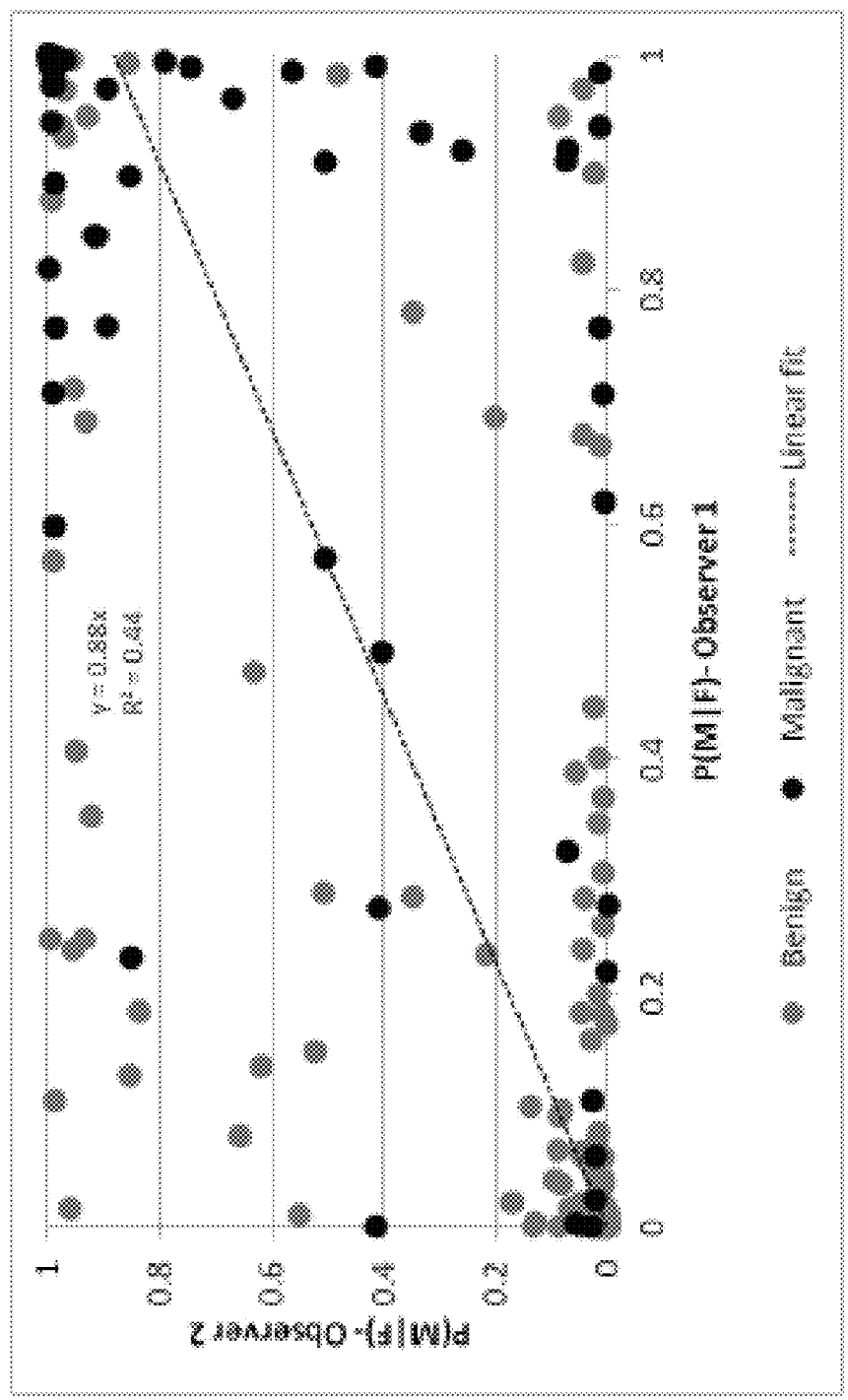
FIG. 5 is a graph illustrating a distribution of assessments as identified by two human observers as well as the accuracy of such identifications in accordance with aspects of the invention.
Figure 6:
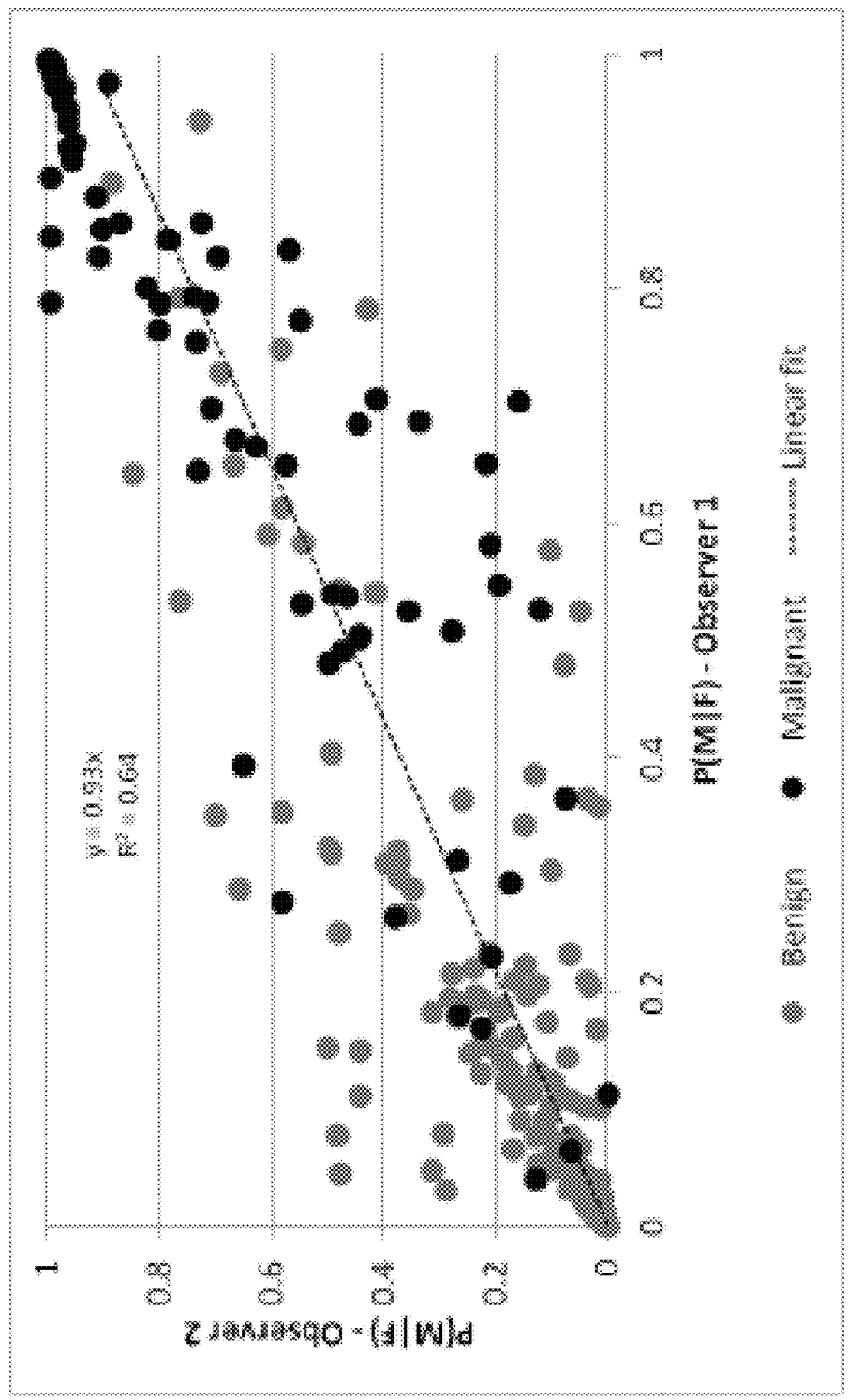
FIG. 6 is a graph illustrating a distribution of assessments, and the accuracy thereof, as identified by two human observers in accordance with the method of FIG. 1.

Some of the benefits of employing adaptive learning analysis are depicted in FIGS. 5 and 6. In FIG. 5 we plot the estimate of the a posteriori probability P(M|F) engendered by Observer 1 versus that for Observer 2, these probability estimates obtained by using the Naive Bayes procedure on the visual features generated by the two observers for each case. In FIG. 6 we plot the revised estimates of the two a posteriori probabilities P(M|F) obtained by AdaBoost by adaptively boosting visual features for the two observers with computer-identified features for each image. Without boosting there is a marked difference between the probability estimates of the two observers. The dotted line in the figure shows the linear (y=mx) least square fit of the data with $R^2$ of 0.44. The concordance correlation coefficient ($p_c$), estimating the degree to which pairs of observations fall on the 45° line through the origin was 0.80. After AdaBoosting the probability estimates of the two observers were uniformly distributed and became better correlated with $R^2$ of 0.64 and $p_c$ of 0.93 (FIG. 6). The difference between the un-boosted and boosted groups for both measures, $R^2$ (p<0.006) and $p_c$ (p<0.0001), was significant. These figures illustrate a key feature that adaptive boosting results in a greater consensus with a concomitant reduction in variability across observers.

Figure 7:
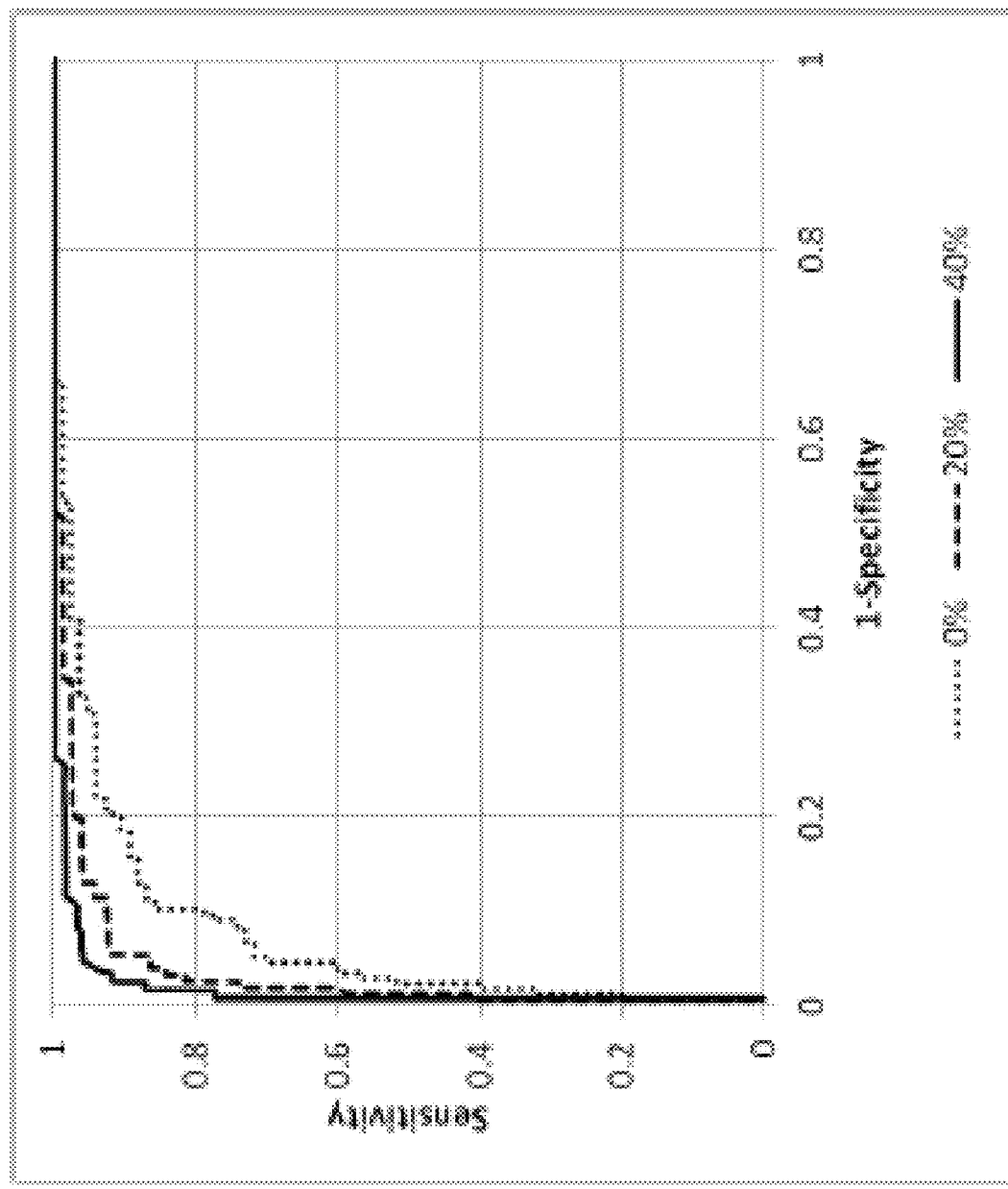
FIG. 7 is a graph illustrating operating curves at different drop rates according to aspects of the invention.

FIG. 7 shows the effect of using a banded ambiguity threshold range where the assessments within the low confidence threshold band are dropped and the diagnostic decision is postponed for additional testing due to low diagnostic performance within the band. The ROC curves for three drop rates ranging from 0% to 40% show a uniform improvement in diagnostic performance with increase in drop rate. Indeed, as the drop rate increases the curves converge towards unit sensitivity and specificity.

Figure 8:
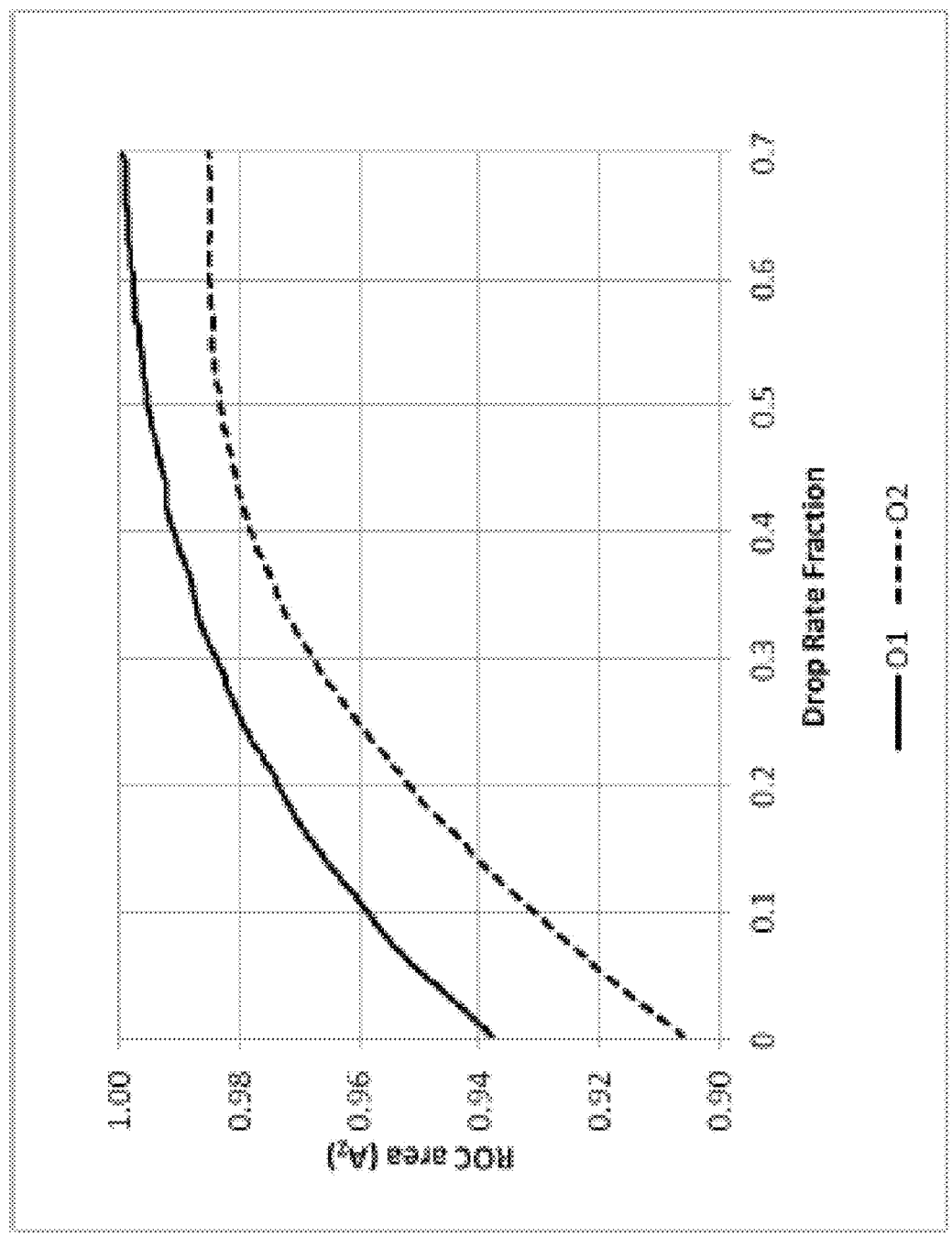
FIG. 8 is a graph illustrating the effect of the drop rate on diagnostic performance according to aspects of the invention.

In FIG. 8 the diagnostic performance for each observer for the AdaBoost classifier as a function of the drop rate. The area under the ROC curve increases monotonically with drop rate for both observers (though performance on the feature set engendered by Observer 1, referred to as O1 in this figure, dominates at all drop rates). The increase, however, is nonlinear with rapid improvement initially moderating to a more gradual improvement at drop rates above 20%. Eventually, the curves plateau with minimal benefits from further increases in drop rates above 50%. A 20% drop rate provides a reasonable compromise between drop rate and performance improvement; at this drop rate the ROC area under the curve increases from 0.937±0.018 to 0.974±0.012 for Observer 1 and 0.906±0.023 to 0.952±0.017 for Observer 2. In both cases rather dramatic improvement in performance at a moderate cost in terms of assessments identified for further evaluation.

Figure 9:
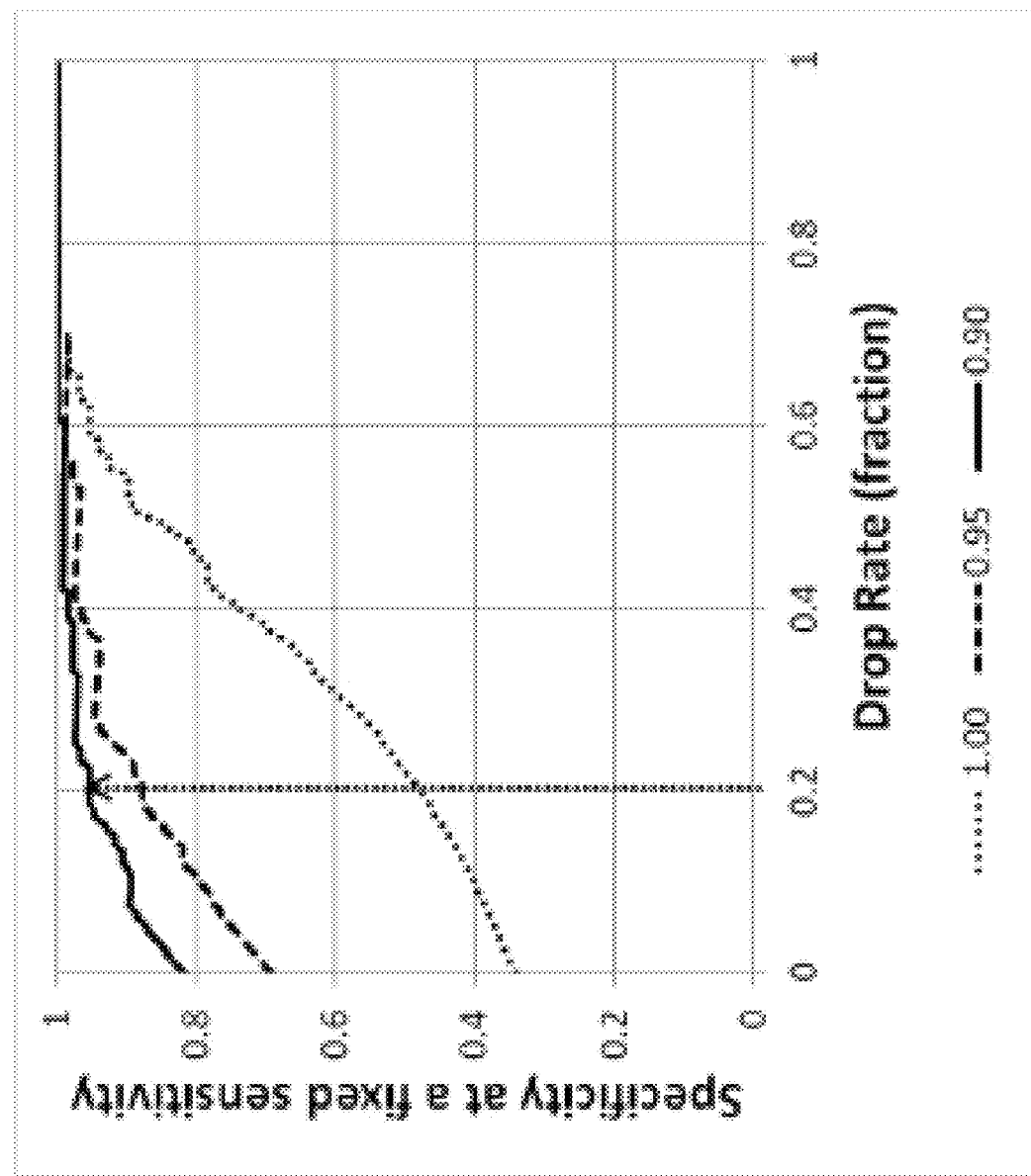
FIG. 9 is a graph illustrating the change in specificity with drop rate at different fixed specificity values in accordance with aspects of the invention.

The change in specificity at a fixed sensitivity for different drop fractions is shown in FIG. 9. In this example, sensitivity relates to the amount of malignant cases that were correctly determined by the methods tested in this Example to be malignant. For example, here, the sensitivity is the proportion of patients who test positive for breast cancer among those who have breast cancer. In this Example, specificity, on the other hand, relates to the amount of benign cases that were correctly determined by the method tested in this Example to be benign. For example, here, specificity is the proportion of patients who test negative for breast cancer among those who do not have breast cancer. The graph in FIG. 9 illustrates that a user can choose an operation point to achieve different sensitivities and specificities. For example, at a drop rate of 20% (vertical arrow) a specificity of 0.95 can be achieved at a sensitivity of 0.90. For the same drop rate the specificity drops to 0.88 and 0.48 at sensitivities of 0.95 and 1.0, respectively.

Figure 10:
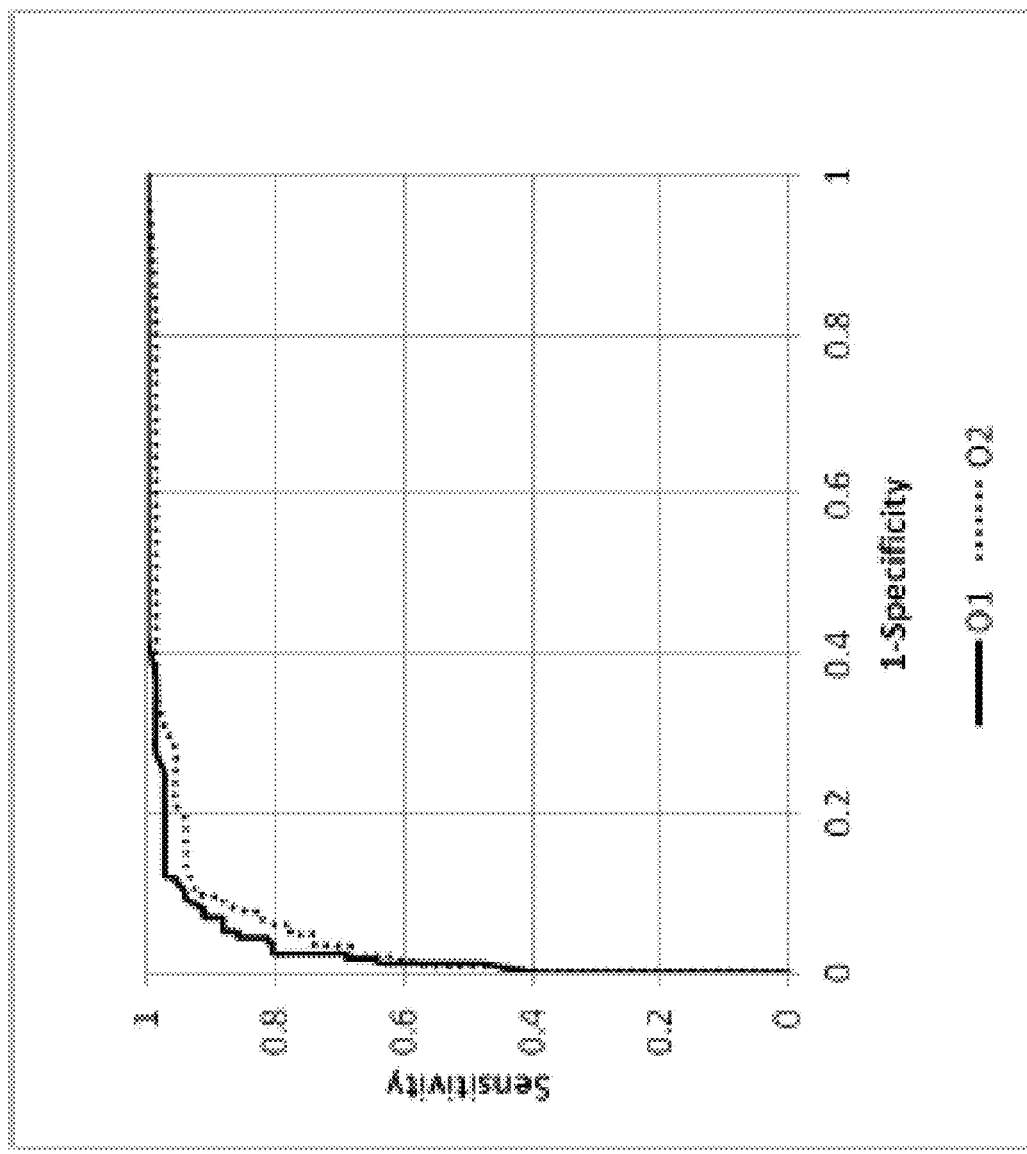
FIG. 10 is a graph illustrating operating curves of the consensus probability estimates according to aspects of the invention.

FIG. 10 shows the results of diagnostic performance when the consensus method between human assessment and computer assessment was used for characterizing low confidence and/or high confidence assessments of the overall risk value, whereby assessments having contradictory risk of malignancy were characterized as low confidence assessments. For both observers the use of computer analysis increased the area under the ROC curves generated by varying the threshold for classification of malignant assessments: for Observer 1 $A_z$ increased to 0. 0.973±0.012 while for Observer 2 $A_z$ increased to 0.955±0.016. The difference of 0.028 in $A_z$ of the two observers was not significant (p=0.0873).

Figure 11:
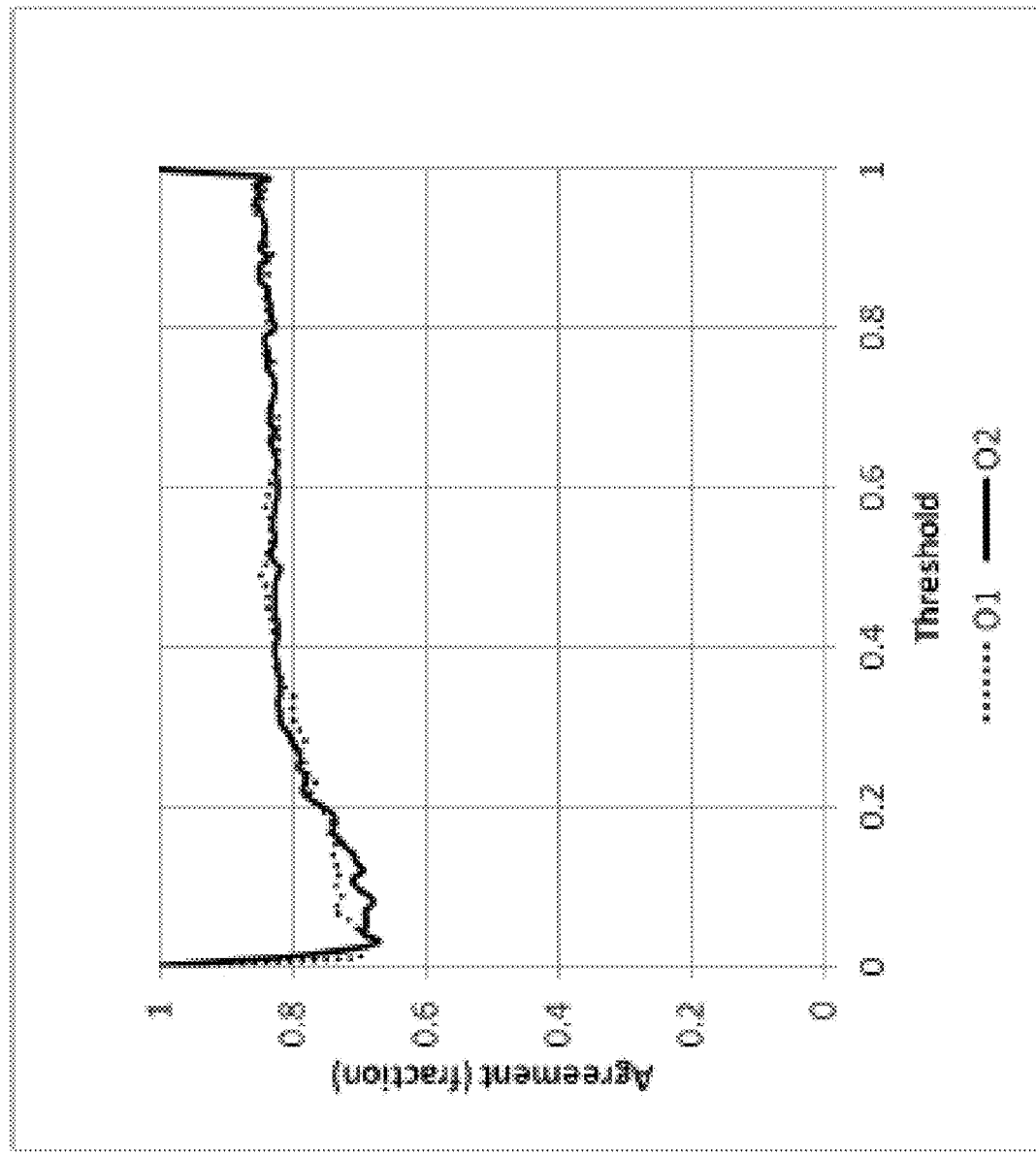
FIG. 11 is a graph illustrating the amount of agreement between human assessment and computer analysis at different probability thresholds in accordance with aspects of the invention.

FIG. 11 shows the results of agreement between the visual and computer analysis as a function of the selected threshold for malignance. The average agreement between visual and computer analysis was 80.9±5.2% and 80.7±5.7% for Observers 1 and 2. The difference was not significant (p=0.77). While the drop rate for a consensus-based method is not directly controllable, FIG. 10 shows that we are operating at about a 20% drop rate over a wide range of thresholds. This suggests that consensus is, in effect, providing a heuristic approximation to a boosting procedure coupled with a 20% drop rate. This interpretation supports the results of Table 2 which shows that the performance of the consensus-based procedure with a drop rate of approximately 20% (inherited from assessments where there is no consensus) is essentially the same as that of the AdaBoost procedure coupled with selective characterization of 20% of the assessments as low confidence (Row E in Table 2 corresponds to a drop rate of 20% in FIG. 8; Rows C and D in Table 1 correspond to a drop rate of 0% in FIG. 4).

This example shows that the diagnostic performance is enhanced using two high accuracy classifiers, such as by human assessment and machine assessment. For example, the use of AdaBoost had an interesting and beneficial effect on the performance of individual observers. Specifically, although the diagnostic performance of two observers on aggregate was high, 0.866 versus 0.924, there were significant differences in the probability estimates on a case by case basis as illustrated by the scatter in FIG. 5. These differences are to be expected given the significant biological variability in the characteristics of breast lesions, the limitations of imaging systems in depicting theses lesions accurately, and differences in observer expertise. However, after AdaBoost was used the probability estimates of the two observers became more uniformly distributed and correlated as shown in FIG. 6. For example, a comparison of FIGS. 4 and 10 shows that the diagnostic performance of the two observers which was noticeably different initially became comparable to one another after assessments of disagreement were identified for further evaluations by the consensus seeking procedure. Although further investigations are needed, these results suggest that AdaBoost could be a useful means to improve consistency in the diagnosis between different observers.

Additionally, the results show that characterizing assessments as low confidence, thereby identifying such assessments for further evaluation, increased the accuracy on assessments for which a prediction is made, at the quantifiable cost of making no prediction on a fraction of assessments, the drop rate. The extent of improvement increased with the increase in the drop rate fraction. Surprisingly, there was a near-perfect classification performance is achievable in a majority of assessments at the cost of a modest drop rate of ambiguous assessments identified as low confidence in a computationally effective manner for additional testing. For example, at a drop rate of 20% an area under the ROC curve of $A_z$=0.975 can be achieved for Observer 1 (FIGS. 7 and 8). A more detailed examination (FIGS. 8 and 9) shows that for sensitivities between 0.90 and 0.95, one can achieve high specificities between 0.975 and 0.88 for the visual feature set generated by Observer 1 coupled with computer-generated features via Adaptive Boosting and selective characterization of low confidence assessments at a 20% drop rate.

TABLE 1

| | Features/Classifier | Observer 1 ($A_z$) | Computer ($A_z$) | Observer 2 ($A_z$) |
|---|---|---|---|---|
| A | Visual features, Naïve Bayes | 0.924 ± 0.021 | | 0.866 ± 0.027 |
| B | Computer features, Logistic Regression | | 0.887 ± 0.025 | |

| | | Observer 1 + Computer | Observer 2 + Computer |
|---|---|---|---|
| C | AdaBoost, Visual Features (A) → Computer features (B) | 0.937 ± 0.018 | 0.906 ± 0.023 |
| D | AdaBoost, Computer Features (B) → Visual Features (A) | 0.936 ± 0.019 | 0.905 ± 0.023 |

Table 2

| | Features/Classifier | Observer 1 + Computer ($A_z$) | Observer 2 + Computer ($A_z$) |
|---|---|---|---|
| A | AdaBoost, Visual Features (A) → Computer features (B), Drop Rate 20% | 0.975 ± 0.018 | 0.956 ± 0.023 |
| B | Consensus, Visual Features ↔ Computer Features, Drop Rate ~20% | 0.973 ± 0.012 | 0.955 ± 0.016 |

Example 2

For illustrative purposes, suppose that there are 200 assessments with 100 benign and 100 malignant and that the distribution of malignant and benign assessments is the same in the sub-sample of assessments characterized as low confidence. Thus, at a 20% drop rate there will be 80 assessments apiece of malignant and benign assessments in the retained subpopulation of 160 high confidence assessments and 20 assessments apiece of malignant and benign assessments in the low confidence subpopulation of 40 assessments (presumed to all be sent for a biopsy). In the high confidence group, if we operate at 80% specificity we obtain a sensitivity (true positive fraction) of 98% from the middle curve of FIG. 7 leading to 2 missed malignant assessments (rounded up from 1.6) out of the total of 80 in this group. This is the regrettable false negative rate at this level of specificity. At an operational point of 80% specificity, 16 of the 80 benign assessments in the high confidence group are misdiagnosed (false positives) and together with the 20 low confidence benign assessments this leads to 36 unnecessary biopsies out of a total of 134 biopsies performed with 2 missed malignant assessments (also sometimes referred to as cases) (Table 3).

To compare this procedure with operation without characterizing assessments as low confidence for further evaluation, we must function at the same true positive rate (sensitivity 98%) leading to 2 missed malignant assessments. As FIG. 7 illustrates, the corresponding specificity for this operating point for the lowest curve (representing no characterization and further evaluation of low confidence assessments) is somewhere between 0.4 to 0.50 due to the fact the curve is very flat at high sensitivities. At a sensitivity of 0.98 and a specificity of 0.45, for definiteness, there will be 55 unnecessary biopsies out of the 153 biopsies performed again with 2 missed malignant assessments (Table 3). Thus, keeping the false negative rate low at 2%, characterizing and further evaluating low confidence assessments would reduce the number of unnecessary biopsies from 55 to 36 (a reduction of 35%).

Our analysis in this example is for illustrative purposes to demonstrate the scope for reduction in the number of unnecessary biopsies at a very low false negative rate. Many factors affect the actual gains in practice. In Example 1, there were two benign masses for every malignant case. If this a priori information is taken into consideration the benefit is even greater than in our numerical example: for 2 missed malignancies, there are 34 unnecessary biopsies out of 99 biopsies performed for the low confidence assessments compared to 73 unnecessary biopsies out of 139 biopsies performed when there was no characterizing the confidence of the case. Similarly, the benefits will be even greater than in this Example if malignant lesions, which are often more difficult to characterize, are present in larger numbers in the ambiguous low group that is identified as a low confidence assessment.

TABLE 3

| 20% prune rate | | | |
|---|---|---|---|
| High Confidence Group | | Low Confidence Group | |
| Malignant cases 80 Sensitivity = 0.98 | Benign cases 80 Specificity = 0.8 | Malignant cases 20 | Benign cases 20 |
| 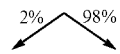 | | 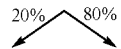 | |

TABLE 3-continued

| # of cases | False + ive 2 | True + ive 78 | False + ive 16 | True + ive 64 | No diagnosis 20 | No diagnosis 20 |
|---|---|---|---|---|---|---|
| Action | No biopsy | Biopsied | Biopsied | No biopsy | Biopsied | Biopsied |
| Result | Missed malignancy | Necessary biopsies | Unnecessary biopsies | Biopsies saved | Necessary biopsies | Unnecessary biopsies |

No pruning

| | Malignant cases 100 Sensitivity = 0.98 | | Benign cases 100 Specificity = 0.45 | | Malignant cases 0 | Benign cases 0 |
|---|---|---|---|---|---|---|

2% / 98%   55% / 45%

| # of cases | False + ive 2 | True + ive 98 | False + ive 55 | True + ive 45 | 0 | 0 |
|---|---|---|---|---|---|---|
| Action | No biopsy | Biopsied | Biopsied | No biopsy | | |
| Result | Missed malignancy | Necessary biopsies | Unnecessary biopsies | Biopsies saved | | |

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A machine implemented method for ultrasound diagnosis, the steps comprising:
   determining, by a computing device, a first risk of malignancy based on data indicative of a human assessment of a first set of features of one or more, ultrasound images of a target;
   determining, by the computing device, a second risk of malignancy based on a second set of features of the one or more ultrasound images, wherein the second set of features are automatically determined by a computer-implemented feature extraction process;
   training, by the computing device and by utilizing a training data set, a classifier, wherein the classifier is selected to match characteristics of either one of or both of the first set of features or the second set of features;
   determining, by the computing device, at least one overall risk value indicative of malignancy based on applying an adaptive learning analysis and the trained classifier to the first risk of malignancy and the second risk of malignancy, wherein the adaptive learning analysis and the trained classifier determine the overall risk value based on combining the first risk of malignancy and the second risk of malignancy and adjusting for a combination one or more weight values applied to the first set of features and the second set of features;
   characterizing, by the computing device, the at least one overall risk value as one of a high confidence assessment or a low confidence assessment.

2. The method of claim 1, further comprising if the overall risk value is characterized as a low confidence assessment, indicating a further evaluation of the target.

3. The method of claim 2, wherein the further evaluation of the target includes one or more of a biopsy and additional imaging.

4. The method of claim 1, wherein the characterizing step includes comparing the at least one overall risk value to an ambiguity threshold range, and wherein, if the at least one overall risk value falls within the ambiguity threshold range, characterizing the at least one overall risk value as a low confidence assessment.

5. The method of claim 1, wherein the second set of features includes at least one feature selected from the group consisting of grayscale, shape, coarseness of a margin, texture of a lesion, information based on Doppler effects, and elastography.

6. The method of claim 1, wherein the second set of features are analyzed by partitioning the target into sectors and comparing the sectors of the target.

7. The method of claim 6, wherein segmentation of the target is accomplished by automated, semi-automated, or manual tracing of the target.

8. The method of claim 1, wherein the classifier is selected from the group consisting of a logistic regression classifier, Naive Bayes classifier, continuous, ordinal, nominal, spatial, and frequency.

9. The method of claim 1, wherein applying the adaptive learning process comprises employing adaptive boosting to analyze either one of or both of the first set of features and the second set of features.

10. The method of claim 1, wherein the overall risk value is based on three or more sets of features of one or more ultrasound images of the target.

11. An ultrasound diagnosis apparatus employing the method of claim 1.

12. A system for diagnosing a tumor using an imaging scan of a target comprising:
   an imaging system configured to perform an imaging scan of a target and to obtain imaging information regarding the target; and
   a processing system configured to:
      receive data indicative of a human assessment of the imaging information, wherein the human assessment of the imaging information is based on a first set of features of the imaging information;
      determine a second set of features of the imaging information, wherein the second set of features are automatically determined by a computer-implemented feature extraction process;
      train, by utilizing a training data set, a classifier, wherein the classifier is selected to match characteristics of either one of or both of the first set of features or the second set of features; and determine an overall risk value indicative of a risk of malignancy based on applying an adaptive learning analysis and the trained classifier to the human assessment of the first set of features and an automated assessment of the second set of features, wherein the adaptive learning analysis and the trained classifier determine the overall risk value based on combining the data indicative of the human assessment and the automated assessment and adjusting for a combination one or more weight values applied to the first set of features and the second set of features.

13. The method of claim 1, wherein the adaptive learning process comprises:

determining a definitiveness of one or more of the first risk of malignancy and the second risk of malignancy; and adjusting one or more of the weight values based on the definitiveness.

14. The method of claim 1, wherein the adaptive learning process determines a first classifier based on the first set of features and a second classifier based on the second set of features, and wherein combining the first risk of malignancy and the second risk of malignancy comprises adjusting a weighting of the first classifier separately from adjusting a weighting of the second classifier.

* * * * *

UNITED STATES PATENT AND TRADEMARK OFFICE
CERTIFICATE OF CORRECTION

| | | |
|---|---|---|
| PATENT NO. | : 11,071,517 B2 | Page 1 of 1 |
| APPLICATION NO. | : 15/341269 | |
| DATED | : July 27, 2021 | |
| INVENTOR(S) | : Sehgal, Jr. et al. | |

It is certified that error appears in the above-identified patent and that said Letters Patent is hereby corrected as shown below:

In the Claims

Under Column No. 15, Line no. 34, Claim 1, Replace:
"one or more, ultrasound"
With:
-- one or more ultrasound --

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*